United States Patent [19]

Bodart

[11] 4,424,277

[45] Jan. 3, 1984

[54] METHOD FOR THE DETERMINATION OF NITRATE IONS

[75] Inventor: Detlef E. Bodart, Darmstadt, Fed. Rep. of Germany

[73] Assignee: Merck Patent Gesellschaft Mit Beschränkter Haftung, Darmstadt, Fed. Rep. of Germany

[21] Appl. No.: 324,369

[22] Filed: Nov. 24, 1981

[30] Foreign Application Priority Data

Nov. 26, 1980 [DE] Fed. Rep. of Germany ....... 3044433

[51] Int. Cl.$^3$ ...................... G01N 21/78; G01N 31/22
[52] U.S. Cl. .................................................. 436/110
[58] Field of Search ........................... 436/110; 422/56

[56] References Cited

U.S. PATENT DOCUMENTS 3,897,214  7/1975  Lange et al. ........................... 422/56
4,003,706  1/1977  Szekely ............................... 436/110

OTHER PUBLICATIONS

Chemical Abstracts–9th Collective, 1972–1976 Chem Substance Index pp. 7609CS, 7664CS and 7665CS.
Ormerod, Chemical Abstracts, vol. 67, 1967, No. 5548c.
Gawargious, "The Determination of Nitro and Related Functions", Academic Press, London and New York, 1973, pp. 78–105, Scientific Library.

Primary Examiner—Arnold Turk
Attorney, Agent, or Firm—Millen & White

[57] ABSTRACT

A method for the colorimetric determination of nitrate ions comprises mixing the sample to be investigated with concentrated sulfuric acid and adding a reagent which initiates coloration, the reagent being a compound of the general formula $RO-C_6H_4-C_6H_4-OR$, wherein R is H or substituted or unsubstituted $C_{1-6}$ alkyl. A reagent and kit for colorimetric nitrate determination are also provided.

12 Claims, No Drawings

METHOD FOR THE DETERMINATION OF NITRATE IONS

BACKGROUND OF THE INVENTION

This invention relates to a method, a reagent and a kit for the colorimetric determination of nitrate ions in aqueous solutions.

Nitrate is an anion which occurs frequently and for which there are relatively few determination possibilities. The only processes which are of importance are those of the colorimetric type, but even these are not very satisfactory in comparison with those for other ions. For this reason, attempts have often been made in the past to reduce nitrate ions to nitrite or ammonium ions, for which there are good color reactions. However, this operation cannot be carried out in a reproducible manner in the context of a rapid cold colorimetric method.

All the color reactions suitable for the direct determination of nitrate ions require concentrated sulfuric acid as a reaction medium. This acid can be only partly replaced by other mineral acids which, however, are also very strong. Under these conditions, nitrate is capable of oxidizing or nitrating certain organic compounds dissolved in the acid. Both reaction variants have been known for over a century, and thus belong to the oldest detection methods still used today for nitrate ions.

Oxidation reactions, for example with brucine (orange product) or diphenylamine (blue product) have the advantage of a clear reaction contrast, but they have the disadvantage of not being very selective, since other ions, for example chloride in sea water, likewise have an oxidizing action under these conditions. Nitration reactions of phenols lead to nitrophenols, which are always yellow. The higher selectivity of these reactions, although still hardly sufficient for application in practice, is counterbalanced by the yellow reaction colors, the differences in intensity of which the eye can differentiate only with difficulty.

It was already known, from *Liebigs Annalen der Chemie*, 207, 335 (1881) that a blue coloration is obtained when 4,4′-dihydroxybiphenyl (4,4′-biphenol) is introduced into concentrated sulfuric acid in the presence of nitrous fumes. In *Z. anal. Chem.*, 98, 227 (1934), there is an indication that aromatic substances containing hydroxyl groups can be used for the detection of nitrate ions in concentrated sulfuric acid, but that this method is not particularly sensitive. However, it has not as yet been possible to develop a quantitative test for the determination of nitrate ions on this basis.

OBJECTS OF THE INVENTION

Accordingly, one object of the present invention is to provide a method for the determination of nitrate ions, with which very small nitrate contents can be reliably detected in a reproducible manner.

Another object of the invention is to provide a reagent suitable for use in the present method.

A further object of the invention is to provide a kit for colorimetric nitrate ion determinations.

Upon further study of the specification and appended claims, further objects and advantages of this invention will become apparent to those skilled in the art.

SUMMARY OF THE INVENTION

These and other objects of the invention are achieved by providing a method for the colorimetric determination of nitrate ions, comprising admixing a sample with concentrated sulfuric acid and a color-generating reagent having the formula $RO-C_6H_4-C_6H_4-OR$, wherein R is H or substituted or unsubstituted $C_{1-6}$ alkyl.

In a composition of matter aspect, a color-generating reagent is provided for colorimetric nitrate ion determinations, consisting essentially of 0.1-5% by weight of a compound having the formula $RO-C_6H_4-C_6H_4-OR$, wherein R is H or substituted or unsubstituted $C_{1-6}$ alkyl, in an organic solvent, said solvent being dimethylsulfoxide, dimethylformamide, acetone, dioxane, ethanol, tetrahydrofuran, pyridine, propylene carbonate, ethylene glycol isopropyl ether or acetic acid.

Alternatively, the reagent is provided as an admixture of 1-99% by weight of the foregoing compound with 1-99% by weight of an alkali metal phosphate, preferably trisodium phosphate dodecahydrate.

A kit for colorimetric nitrate ion determinations comprises one of the foregoing reagents and a container of 24-36 N sulfuric acid.

DETAILED DISCUSSION

Surprisingly, it has been found that 4,4′-biphenols and their alkyl ethers give color reactions with nitrate ions in the presence of concentrated sulfuric acid, these color reactions fulfilling the simultaneous requirements of reaction contrast and selectivity.

In the method of the invention for the colorimetric determination of nitrate ions, the sample to be investigated is mixed with concentrated sulfuric acid and a reagent which generates coloration. The color-generating reagent is a compound having the formula $RO-C_6H_4-C_6H_4-OR$, wherein R is H or substituted or unsubstituted $C_{1-6}$ alkyl.

A precondition for obtaining a blue color reaction is that the RO groups be in the para-positions of the biphenyl nucleus. The radical R can be H or $C_{1-6}$ alkyl, e.g., methyl, ethyl, propyl, i-propyl, butyl, i-butyl, pentyl, i-pentyl, hexyl or i-hexyl. A preferred reagent is 4,4′-bianisole, where R is methyl. It is also possible for the alkyl groups to be substituted, e.g., by carboxyl groups, ester groups or other groups which do not interfere with the color-generating reaction. Substitution on the biphenyl nucleus is more likely to impair the reaction.

Precise matching of the individual parameters is necessary in order to prepare the blue reaction product. Dosages of the reagent which are too low lead to colorless blank values. However, in the presence of nitrate ions, they lead to mixed colors which comprise a blue compound and the corresponding yellow nitrophenol and are stable for only a short time and then change into the yellow of the pure nitrophenol. Reproducible nitrate determinations require an excess of reagent, but this results in a slightly greenish blank value. The permissible upper limit of the reagent concentration is determined by its solubility. Suitable reagent concentrations in the mixture being measured are in the range of about 0.001-0.2% by weight. For the preferred 4,4′-bianisole, a concentration of about 0.005-0.08% by weight, preferably about 0.04% by weight, is suitable.

Both solutions and powders, the latter optionally in the form of a mixture with a solid carrier, have proved advantageous forms for dispensing the reagent. Suitable solvents for solutions of the reagent should be miscible with concentrated sulfuric acid, e.g., the organic solvents dimethylsulfoxide, dimethylformamide, ketones, dioxane, ethanol, tetrahydrofuran, pyridine, propylene carbonate, ethylene glycol isopropyl ether and acetic acid. The concentration of the reagent solution and the solvent chosen are selected for convenience in dispensing, so that the final concentration of reagent in the sample mixture is in the proper range. Preferred solvents include propylene carbonate and ketones such as acetone and ethyl methyl ketone.

A reagent for colorimetric nitrate ion determination advantageously contains 0.1–5% by weight of the biphenol or biphenol ether in one of the foregoing organic solvents.

Suitable carrier substances for powder mixtures include inert solids, e.g., alkali metal phosphates. A preferred carrier is trisodium phosphate dodecahydrate. An alternative reagent for colorimetric nitrate ion determination is an admixture of 1–99% by weight of the biphenol or biphenol ether and 1–99% by weight of the alkali metal phosphate.

The color reaction is carried out at a sulfuric acid concentration of about 24–36 N, preferably about 33–35 N. Higher concentrations give paler colors, and lower concentrations lead initially to pale, cloudy colors, but after the mixture has stood for about one hour these become deep blue, fast colors. However, the solubility of the biphenols and ethers thereof decrease greatly in the lower sulfuric acid concentration range, so that the cloudiness continuously increases and, after the mixture has stood for some days, an ultramarine blue coagulate separates out. Below a concentration of about 23 N, a colorless solution clouded by white unreacted biphenol or biphenol ether is obtained.

Instead of sulfuric acid, it is also possible to use a mixture of sulfuric acid and phosphoric acid. Up to about 70% by volume of concentrated phosphoric acid is suitable in such a mixture.

A kit for use in the present method comprises a container of 24–36 N sulfuric acid, preferably 33–35 N, and a container of the solution of color-generating regent in an organic solvent or of the solid reagent, either alone or in combination with an alkali metal phosphate carrier. Optionally, the kit can include a calibrated color scale or a calibrated curve for correlating spectrophotometric values with nitrate ion concentrations.

Nitrate ions are determined by adding sulfuric acid to the sample solution to be investigated and cooling the mixture to room temperature. The color-generating reagent is then added and the components are mixed thoroughly. It is also possible to add the reagent first and then add the sulfuric acid to the sample solution. The reaction is complete after a few minutes, and can be evaluated either visually with the aid of a color scale or photometrically.

A color gradation which can very easily be differentiated optically is obtained if the nitrate ions in the sample solution to be investigated are present in a concentration range of about 0.15–3.5 mg/l (1 mg/l≃1 ppm). The concentration of nitrate ions in the final reaction mixture is advantageously adjusted to this range. This can easily be effected by adjusting the relative volumes of the sample and the concentrated acid, as a function of the approximate range of nitrate ion content in the sample.

The concentration range which is of interest, e.g., in the analysis of water from industrial areas is about 10–200 ppm of nitrate ions in the water. In order to achieve an optimum color gradation, the ratio of water sample to sulfuric acid in this case would have to be adjusted by a factor of 1:60, that is, the mixture to be measured should be prepared by mixing 0.1 ml of water sample and 6.0 ml of sulfuric acid to ensure an optimum color gradation. A slightly diluted sulfuric acid (about 93%=34.7 N) is advantageously used to establish the desired final concentration of sulfuric acid.

A measurement range of 2–40 ppm of nitrate ions is of interest where water with a particularly low nitrate content is required, e.g., in the brewing industry. Here, a more sensitive color system is achieved by combining, e.g., 6 ml of 96% (36 N) sulfuric acid with 0.5 ml of water sample.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

6 ml of concentrated sulfuric acid (a mixture of 250 ml of 96% sulfuric acid and 15 ml of demineralized water) are added to 0.1 ml of a water sample, which can contain between 10 and 200 ppm of nitrate ions, in a test tube and the mixture is cooled to room temperature. 6 drops (0.17 ml) of a 0.4% solution of 4,4'-bianisole in a 2:1 mixture of propylene carbonate and ethyl methyl ketone are then added and the components are mixed. After 3 to 5 minutes, a clear color gradation from pale light-green to deep blue, depending on the content of nitrate ions, can be seen, and can be unambiguously correlated with the corresponding nitrate ion content with the aid of a calibrated scale with 8 color values. Analogous results are achieved if either 4,4'-dipropoxybiphenyl or 4,4'-biphenol is added instead of 4,4'-bianisole.

EXAMPLE 2

6 mol of 96% sulfuric acid are carefully added to 0.5 ml of a water sample, which can contain between 2 and 40 ppm of nitrate ions. After mixing the components and cooling the mixture to about 20° C., 0.1 mg of a 5% mixture of 4,4'-bianisole in trisodium phosphate dodecahydrate is dissolved in the mixture with slight shaking. After 3 to 5 minutes, a clear color gradation from pale light-green to deep blue, depending on the content of nitrate ions, can be seen, and can be evaluated either with the aid of a calibrated color scale or by spectrophotometry. For spectrophotometric evaluation, the reaction mixture is measured against a simultaneously prepared blank sample in a cell 10 mm thick at 730 nm in a spectrophotometer. The concentration of nitrate ions is read off, with the aid of the extinction value measured, on a calibration curve which has been obtained beforehand with solutions with accurately known contents of nitrate ions.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for the quantitative colorimetric determination of nitrate ions, comprising admixing a sample with concentrated sulfuric acid and a color-generating reagent having the formula 4,4'-RO—$C_6H_4$—$C_6H_4$—OR, wherein R is substituted or unsubstituted $C_{1-6}$ alkyl, said color-generating reagent being present in an amount effective to produce a quantitative coloration; and correlating the color of the resultant solution with a calibrated reference standard.

2. A method according to claim 1, wherein the sulfuric acid is used in a concentration of about 24-36 N.

3. A method according to claim 1, wherein the color-generating reagent is added in the form of a solution in an organic solvent.

4. A method according to claim 1, wherein the color-generating reagent is added in the form of a powder.

5. A method according to claim 1, wherein the sample is first mixed with the sulfuric acid, and the mixture is cooled to about room temperature before the reagent is added.

6. A method according to claim 1, wherein the amount of the color-generating reagent in the mixture being measured is 0.001-0.2% by weight.

7. A method according to claim 2, wherein the sulfuric acid concentration is 33-35 N.

8. A method according to claim 6, wherein the color-generating reagent is 4,4'-bianisole, and the amount is 0.005-0.08% by weight in the mixture.

9. A method according to claim 1, wherein the color-generating reagent is 4,4'-bianisole.

10. A method according to claim 4, wherein the powdered reagent further comprises an alkali metal phosphate.

11. A method according to claim 10, wherein the alkali metal phosphate is trisodium phosphate dodecahydrate.

12. A method according to claim 3, wherein the organic solvent is dimethylsulfoxide, dimethylformamide, acetone, dioxane, ethanol, tetrahydrofuran, pyridine, propylene carbonate, ethylene glycol isopropyl ether or acetic acid.

* * * * *